(12) United States Patent
Wilson et al.

(10) Patent No.: US 8,663,312 B2
(45) Date of Patent: Mar. 4, 2014

(54) INTRAVASCULAR CUFF

(75) Inventors: Robert Foster Wilson, Roseville, MN (US); John Gainor, White Bear Township, MN (US)

(73) Assignee: HLT, Inc., Maple Grove, MN (US)

( * ) Notice: Subject to any disclaimer, the term of this patent is extended or adjusted under 35 U.S.C. 154(b) by 822 days.

(21) Appl. No.: 11/442,371

(22) Filed: May 26, 2006

(65) Prior Publication Data

US 2006/0276874 A1 Dec. 7, 2006

Related U.S. Application Data

(60) Provisional application No. 60/685,433, filed on May 27, 2005, provisional application No. 60/685,349, filed on May 27, 2005, provisional application No. 60/709,595, filed on Aug. 18, 2005.

(51) Int. Cl.
*A61F 2/06* (2013.01)

(52) U.S. Cl.
USPC .................................................. 623/1.15

(58) Field of Classification Search
USPC ............. 623/2.11, 2.38, 1.1, 1.12, 1.15, 1.24, 623/1.26, 2.1, 2.14, 2.17–2.19, 23.68, 900, 623/904, 910, 918, 922; 606/108, 192, 194, 606/213
See application file for complete search history.

(56) References Cited

U.S. PATENT DOCUMENTS

| | | | |
|---|---|---|---|
| 4,056,854 A | 11/1977 | Boretos et al. | |
| 6,015,431 A | 1/2000 | Thornton et al. | |
| 6,168,614 B1 | 1/2001 | Andersen et al. | |
| 6,425,916 B1 * | 7/2002 | Garrison et al. | 623/2.11 |
| 6,652,578 B2 | 11/2003 | Bailey et al. | |
| 6,719,781 B1 | 4/2004 | Kim | |
| 6,893,457 B2 | 5/2005 | Dong | |
| 7,445,630 B2 * | 11/2008 | Lashinski et al. | 623/2.1 |
| 2004/0220664 A1 | 11/2004 | Chobotov | |
| 2004/0260333 A1 | 12/2004 | Dubrul et al. | |
| 2005/0137691 A1 * | 6/2005 | Salahieh et al. | 623/2.11 |
| 2005/0137702 A1 * | 6/2005 | Haug et al. | 623/2.38 |
| 2008/0015671 A1 * | 1/2008 | Bonhoeffer | 623/1.2 |

* cited by examiner

*Primary Examiner* — Thomas McEvoy
*Assistant Examiner* — Jocelin Tanner
(74) *Attorney, Agent, or Firm* — Inskeep IP Group, Inc.

(57) ABSTRACT

An intravascular cuff acts as a lining between a native vessel and an intravascular prosthetic device. During deployment, the ends of the cuff curl back upon themselves and are capable of trapping native tissue, such as valve leaflet tissue, between the ends. The cuff creates a seal between the vessel and the prosthetic, thereby preventing leakage around the prosthetic. The cuff also traps any embolic material dislodged from the vessel during expansion of the prosthetic.

12 Claims, 5 Drawing Sheets

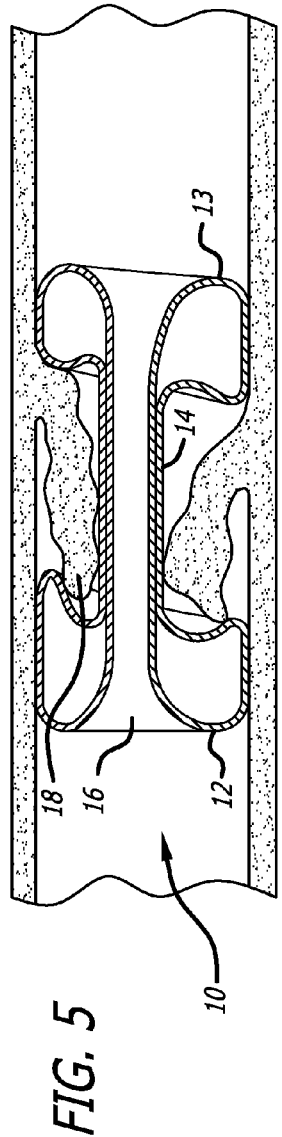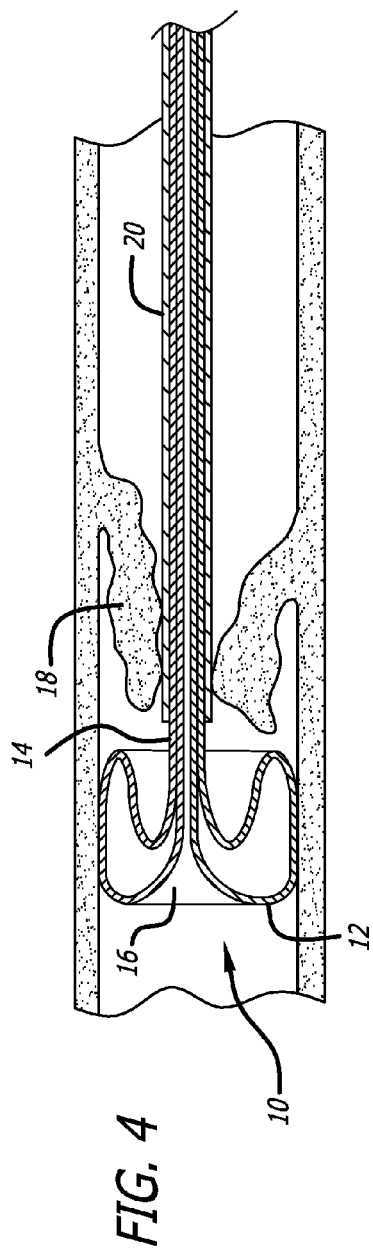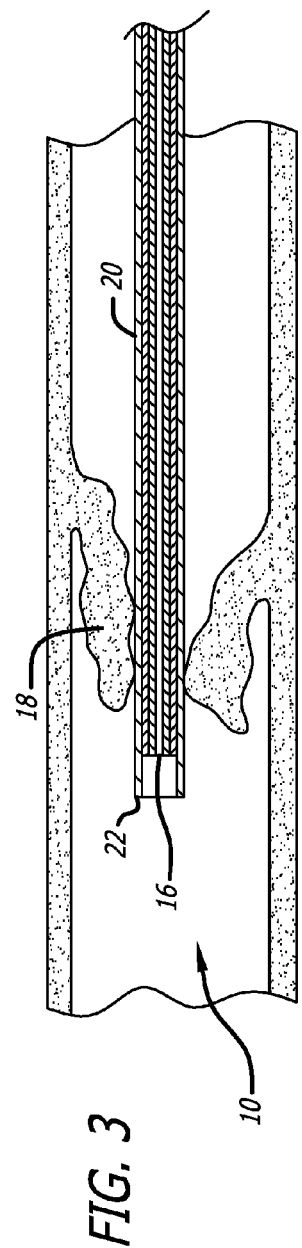
FIG. 5
FIG. 4
FIG. 3

INTRAVASCULAR CUFF

CROSS-REFERENCE TO RELATED DOCUMENTS

This application is related to and claims priority benefit of U.S. Provisional Patent Application Ser. No. 60/685,433, filed May 27, 2005, entitled Intravascular Cuff, by Wilson et al. and is also hereby incorporated by reference herein. This application also incorporates by reference U.S. patent application Ser. No. 11/443,814 entitled Stentless Support Structure filed by Applicant on May 30, 2006 and U.S. Provisional Patent Application Ser. No. 60/685,349, filed May 27, 2005, entitled Stentless Support Structure and U.S. Provisional Patent Application Ser. No. 60/709,595, filed Aug. 18, 2005, entitled Stentless Support Structure.

BACKGROUND OF THE INVENTION

There has been a significant movement toward developing and performing cardiac and other surgeries using a percutaneous approach. Through the use of one or more catheters that are introduced through, for example, the femoral artery, tools and devices can be delivered to a desired area in the cardiovascular system to perform any number of complicated procedures that normally otherwise require an invasive surgical procedure. Such approaches greatly reduce the trauma endured by the patient and can significantly reduce recovery periods. The percutaneous approach is particularly attractive as an alternative to performing open-heart surgery.

Valve replacement surgery provides one example of an area where percutaneous solutions are being developed. A number of diseases result in a thickening, and subsequent immobility or reduced mobility, of valve leaflets. Valve immobility leads to a narrowing, or stenosis, of the passageway through the valve. The increased resistance to blood flow that a stenosed valve presents eventually leads to heart failure and death.

Treating severe valve stenosis or regurgitation has heretofore involved complete removal of the existing native valve followed by the implantation of a prosthetic valve. Naturally, this is a heavily invasive procedure and inflicts great trauma on the body leading usually to great discomfort and considerable recovery time. It is also a sophisticated procedure that requires great expertise and talent to perform.

Historically, such valve replacement surgery has been performed using traditional open-heart surgery where the chest is opened, the heart stopped, the patient placed on cardiopulmonary bypass, the native valve excised and the replacement valve attached. A proposed percutaneous valve replacement alternative method is disclosed in U.S. Pat. No. 6,168,614 (the entire contents of which are hereby incorporated by reference) issued to Andersen et al. In this patent, the prosthetic valve is collapsed to a size that fits within a catheter. The catheter is then inserted into the patient's vasculature and moved so as to position the collapsed valve at the location of the native valve. A deployment mechanism is activated that expands the replacement valve against the walls of the body lumen. The expansion force pushes the leaflets of the existing native valve against the lumen wall thus essentially "excising" the native valve for all intents and purposes. The expanded structure, which includes a stent configured to have a valve shape with valve leaflet supports, is then released from the catheter and begins to take on the function of the native valve. As a result, a full valve replacement has been achieved but at a significantly reduced physical impact to the patient.

However, this approach has decided shortcomings. One particular drawback with the percutaneous approach disclosed in the Andersen '614 patent is the difficulty in preventing leakage around the perimeter of the new valve after implantation. As the tissue of the native valve remains within the lumen, there is a strong likelihood that the commissural junctions and fusion points of the valve tissue (as pushed against the lumen wall) will make sealing of the prosthetic valve around the interface between the lumen and the prosthetic valve difficult.

Other drawbacks of the Andersen '614 approach pertain to its reliance on stents as support scaffolding for the prosthetic valve. First, stents can create emboli when they expand. Second, stents are typically not effective at trapping the emboli they dislodge, either during or after deployment. Third, stents do not typically conform to the features of the native lumen in which they are placed, making a prosthetic valve housed within a stent subject to paravalvular leakage. Fourth, stents can be hard to center within a lumen.

As to the first drawback, stents usually fall into one of two categories: self-expanding stents and expandable stents. Self-expanding stents are compressed when loaded into a catheter and expand to their original, non-compressed size when released from the catheter. Balloon expandable stents are loaded into a catheter in a compressed but relaxed state. A balloon is placed within the stent. Upon deployment, the catheter is retracted and the balloon inflated, thereby expanding the stent to a desired size. Both of these stent types exhibit significant force upon expansion. The force is usually strong enough to crack or pop thrombosis, thereby causing pieces of atherosclerotic plaque to dislodge and become emboli. If the stent is being implanted to treat a stenosed vessel, a certain degree of such expansion is desirable. However, if the stent is merely being implanted to displace native valves, less force may be desirable to reduce the chance of creating emboli.

As to the second drawback, if emboli are created, expanded stents usually have members that are too spaced apart to be effective to trap any dislodged material. Often, secondary precautions must be taken including the use of nets and irrigation ports.

The third drawback is due to the relative inflexibility of stents. Stents rely on the elastic nature of the native vessel to conform around the stent. Stents used to open a restricted vessel do not require a seal between the vessel and the stent. However, when using a stent to displace native valves and house a prosthetic valve, a seal between the stent and the vessel is necessary to prevent paravalvular leakage. Due to the non-conforming nature of stents, this seal is hard to achieve, especially when displacing stenosed valve leaflets.

The fourth drawback is that stents can be hard to center within a lumen. Stenosed valves can have very irregular shapes. When placing a stent within an irregularly shaped, calcified valve, the delivery catheter can become misaligned causing the stent to be delivered to an off-center location, such as between two calcified valve leaflets. Expanding the stent in such a location can result in poor seating against the lumen walls and significant paravalvular leakage or a non-functioning prosthetic valve.

BRIEF SUMMARY OF THE INVENTION

The present invention addresses the aforementioned drawbacks by providing a tubular or toroidal cuff that surrounds a native valve and creates an ideal implantation site for a stent. The cuff is constructed of at least one fine braided strand of a material having super-elastic or shape memory characteristics, such as Nitinol. The cuff is tubular when in an extended configuration within a delivery catheter. When released from the delivery catheter, the ends of the cuff curl back on themselves, trapping the native valve leaflets between the curled ends. The center of the cuff does not expand as much as the ends, thereby leaving a reduced diameter lumen that is ideal for receiving an intravascular device.

BRIEF DESCRIPTION OF THE DRAWINGS

FIGS. 3-7 are cutaway views of a device of the present invention being deployed in a native vessel;

DETAILED DESCRIPTION OF THE INVENTION

Figure 2:
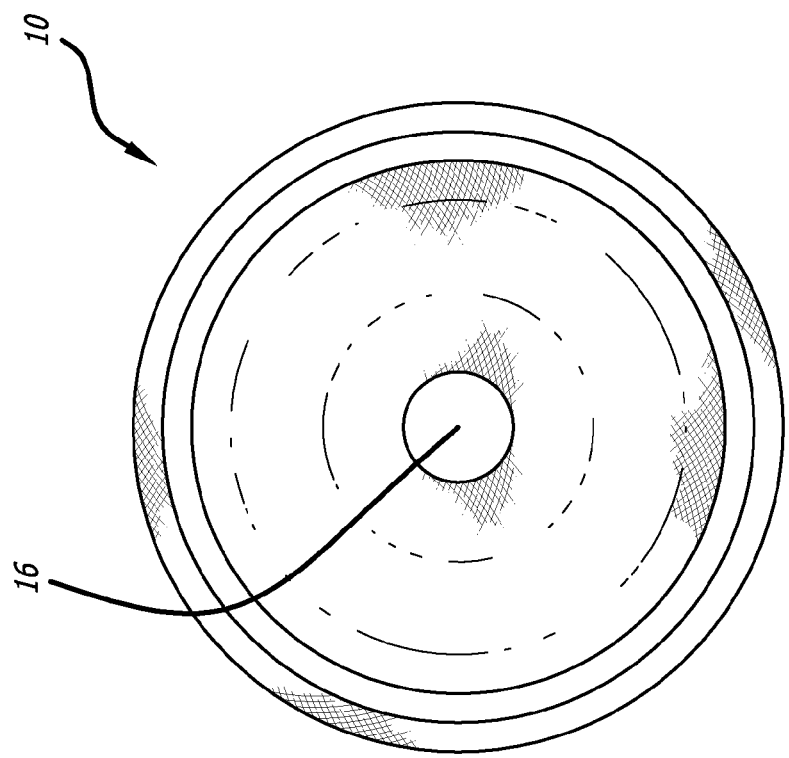
FIG. 2 is an end view of the device of FIG. 1.
Figure 1:
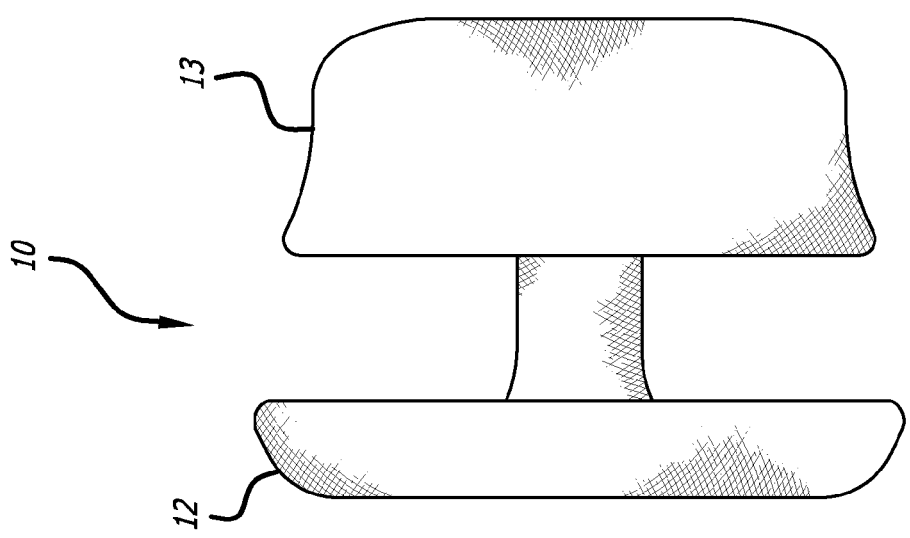
FIG. 1 is a side view of a preferred device of the present invention.

Referring now to the Figures and first to FIGS. 1 and 2, there is shown an intravascular cuff 10 of the present invention. The cuff 10 is shown in its relaxed, expanded configuration and comprises a generally tubular structure having two flared ends 12 and 13 and a narrow tubular body 14. The elongated tube that is used to construct the cuff 10 is formed from at least one braided strand capable of exhibiting superelasticity or shape memory. In one embodiment, the elongated tube is folded in half upon itself such that the first end 12 becomes a folded end and the second end 13 includes a plurality of unbraided strands. The tubular body is thus two-ply. The strand or strands may be fibrous, non-fibrous, multifilament, or monofilament. Nitinol is an example of a preferable material for the strand(s). The strand(s) are braided to allow the device to be expanded longitudinally into a very long, thin tube capable of being placed in a very small delivery catheter. Preferably, the cuff 10 can be inserted into a delivery catheter that is sized 16 Fr or smaller. The braids are tight enough to catch emboli that may be dislodged from a lumen wall, while still allowing the thin, elongated configuration.

The cuff 10 includes a central lumen 16, which extends through the entire cuff 10. The central lumen 16 is sized to receive a delivery catheter for a prosthetic device such as a stent. Preferably, the lumen 16 has ends that flare or mushroom gently, thereby creating a funnel for guiding a delivery catheter into the center of the lumen 16.

FIGS. 1 and 2 show that, even when the cuff 10 is in a radially expanded, relaxed configuration, the lumen 16 is small and very well defined. Thus, when deployed, the mushroom-like ends 12 and 13 expand and conform to the shape of the target vessel lumen while the cuff lumen 16 remains well defined and relatively centered within the cuff 10. Thus, the cuff 10 presents an ideal target and guide for a physician placing a prosthetic valve or stent within the cuff. Preferably, the cuff 10 is radiopaque, making the target it presents even more accessible.

The deployment of the cuff 10 is illustrated in FIGS. 3-7. Beginning with FIG. 3, a cuff 10 is percutaneously delivered to a targeted stenosed valve 18 via a delivery catheter 20. The catheter 20 is advanced until a distal end 22 of the catheter is past the targeted valve 18.

As seen in FIG. 4, the delivery catheter 20 is then retracted relative to the cuff 10. Doing so releases the distal end 12, which immediately flares outwardly. With the end 12 in contact with the vessel walls, the physician may pull gently on the catheter 20 and the cuff 10 to abut the end 12 of the cuff 10 against the stenosed valve 18, thereby ensuring proper placement of the cuff 10.

Figure 7:
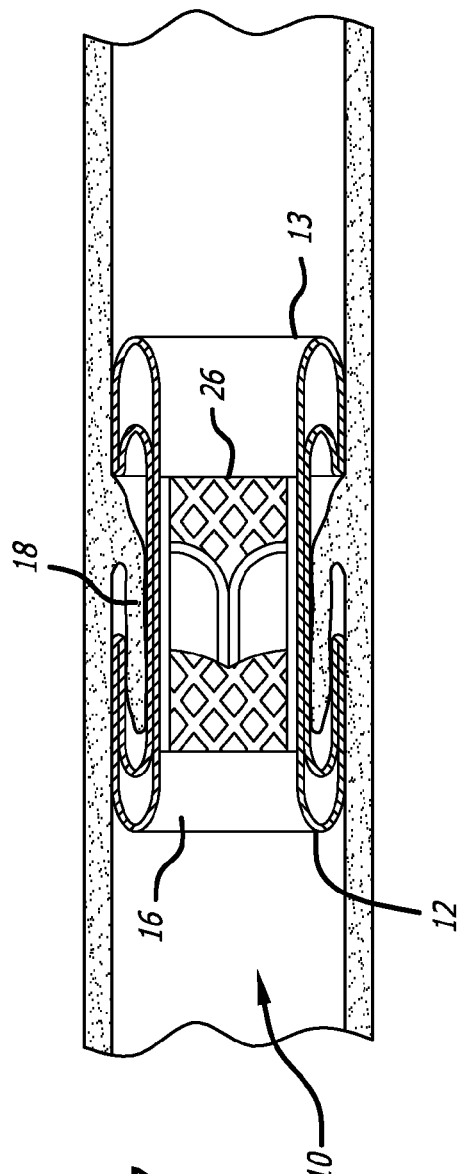
Figure 6:
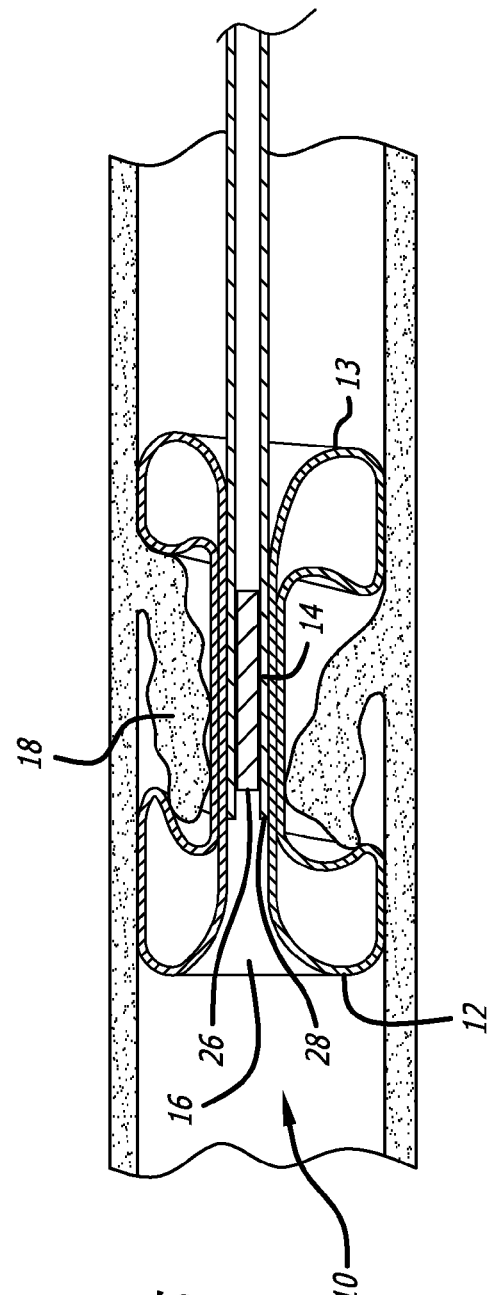

Next, as shown in FIG. 5, the catheter 20 is retracted fully, allowing the proximal end 13 of the cuff 10 to expand against the vessel walls on a proximal side of the stenosed valve 18. The stenosed valve 18 is now completely encased in the braided mesh of the cuff 10, and the cuff is ready to receive a prosthetic device such as a stented prosthetic valve 24 (FIGS. 6 and 7). Notably, despite the irregular shape of the stenosed valve 18, the central lumen 16 of the cuff presents a path through the targeted site and provides an ideal receiving seat for the prosthetic valve 24.

In FIG. 6, the stented prosthetic valve 26 is percutaneously delivered to the cuff 10 via a catheter 28. The catheter 28 is inserted directly into the cuff lumen 16, using the funneled end 13 as a guide.

In FIG. 7, the prosthetic valve 26 is expanded and the catheter 28 removed. Expanding the stented prosthetic 26 necessarily expands the central lumen 16. Doing so causes the cuff 10 to shorten and the flared ends 12 and 13 to fold back further, placing a more secure grip on the stenosed valve 18. Furthermore, any plaque or other material dislodged during the expansion of the prosthetic 26 is trapped by the ends 12 and 13. The cuff 10 provides an optimal seat for the prosthetic 26 and prevents any blood from leaking around the prosthetic valve 26. Over time, the braided strand(s) promote ingrowth, further improving the seal provided by the cuff 10.

Figure 8:
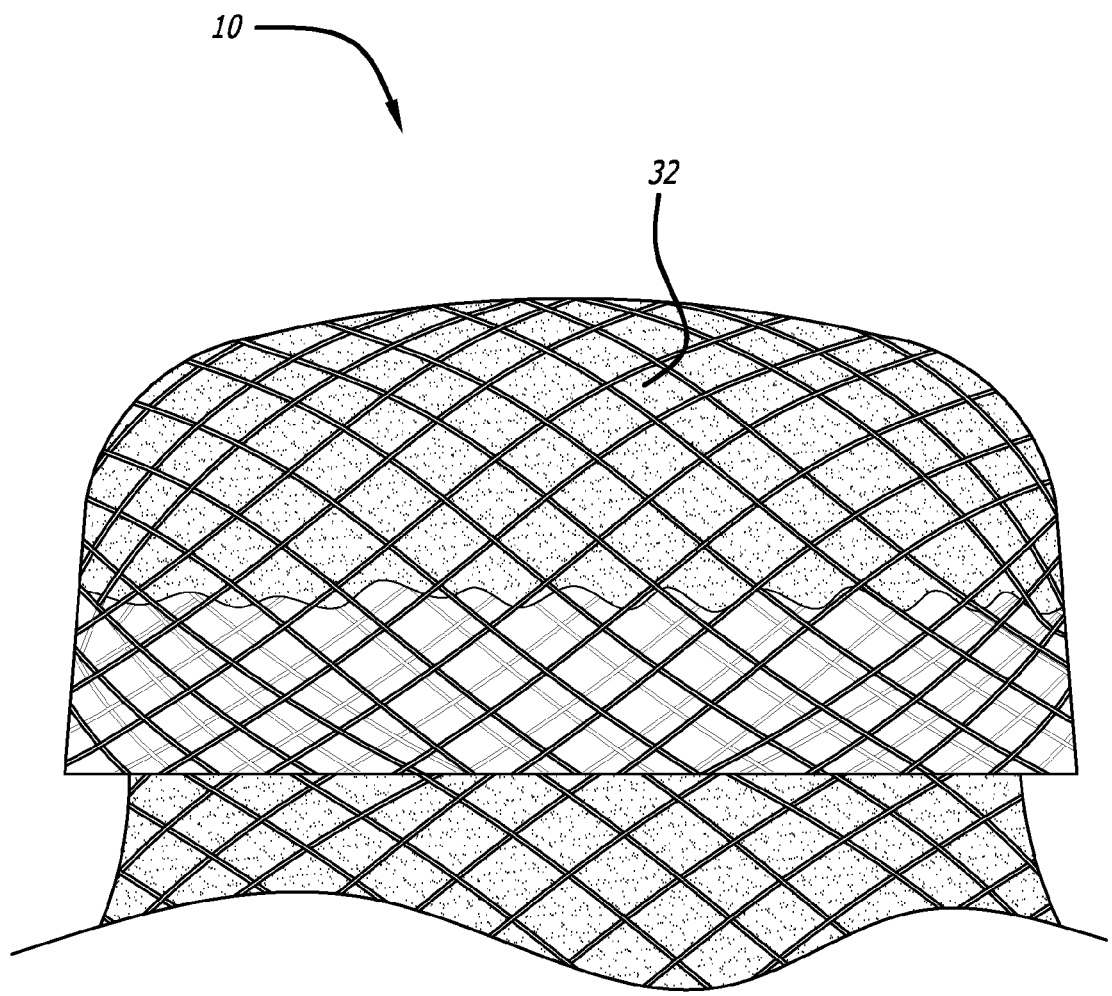
FIG. 8 is a side view of a preferred device of the present invention.

One embodiment of the present invention uses a non-woven fabric to further enhance the seal created between the cuff 10 and the vessel walls. FIG. 8 shows a cuff 10 having a two-ply body with a material 32 trapped between the two layers. The non-woven fabric expands easily such that the expansion characteristics of the cuff 10 are not affected. Additionally, the material 32 may be impregnated with a therapeutic compound. The material 32 can consist of a non-woven material, a woven fabric, a polymer or other material.

Figure 10:
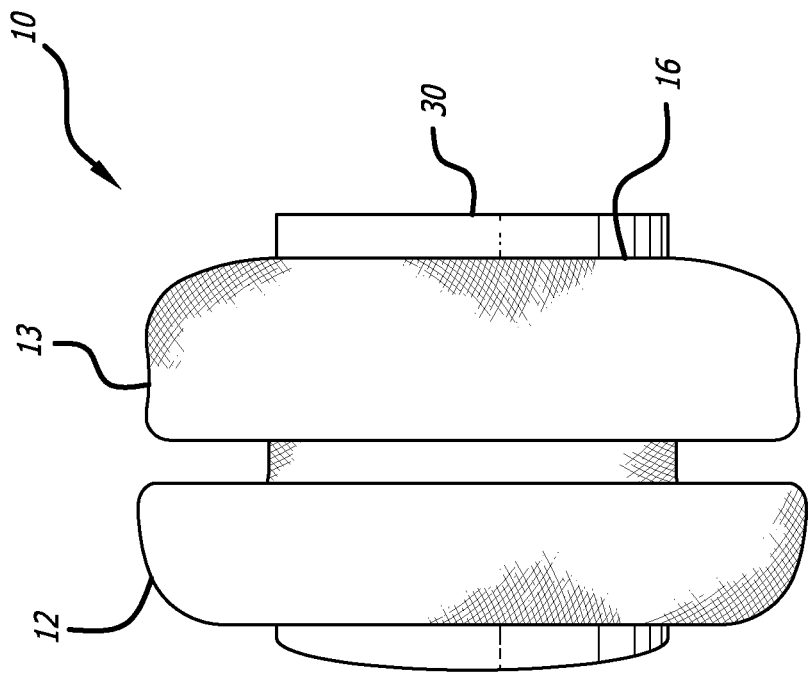
FIG. 10 is a side view of the device of FIG. 1 in an expanded state.
Figure 9:
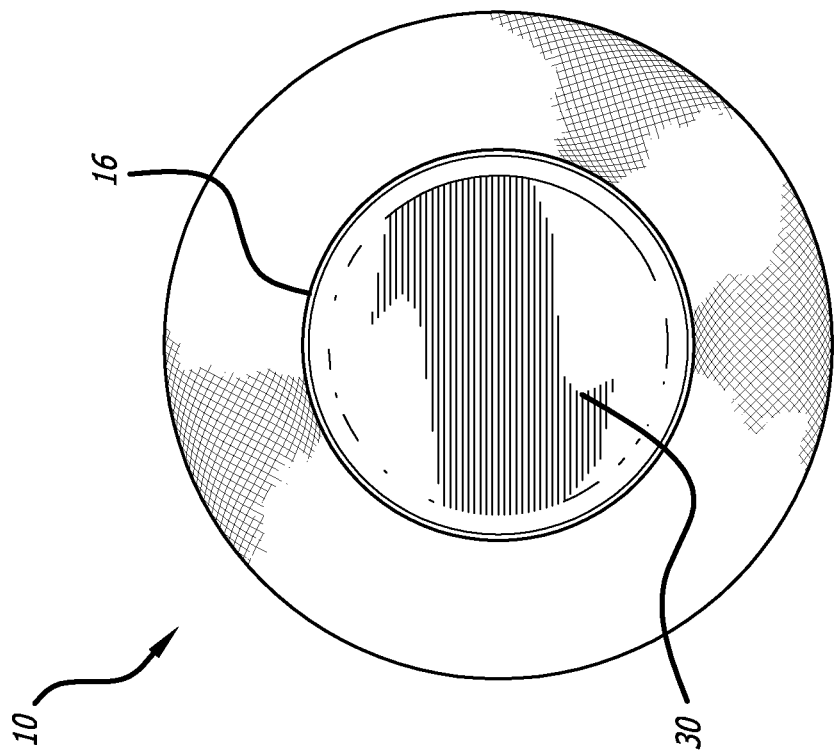
FIG. 9 is an end view of the device of FIG. 1 in an expanded state.

Referring now to FIGS. 9 and 10, the cuff 10 originally depicted in FIGS. 1 and 2 is shown with a plug 30 expanding the central lumen 16 of the cuff 10. This demonstrates how the cuff 10 shortens and the ends 12 and 13 fold back when the lumen 16 is expanded. Expanding the central lumen 16 thus causes the ends 12 and 13 to create a strong grip on native tissues, such as valve leaflets, lodged between the ends 12 and 13.

In another embodiment, on deployment from a catheter, the ends of the elongate tube roll outwardly toward the middle of the device. Alternatively, the end can roll inwardly toward the middle of the device. This action would be facilitated by use of a super-elastic or shape memory material such as Nitinol.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:
1. A method of preventing leakage between a prosthetic valve and a vessel wall comprising:
deploying a self-expanding mesh cuff having at least two-ply in the vessel prior to implanting the prosthetic valve, said mesh cuff including a center body portion and two end portions on either side of the center body portion;

allowing the end portions to expand and form a seal against the vessel wall while the center body portion of said cuff forms inwardly-curving sidewalls;

implanting the prosthetic valve to said inwardly-curving sidewalls after the step of allowing the end portions to expand;

wherein at least one of said end portions mushrooms when expanded such that a gap is created between the plies of the end portions, thereby creating a funnel for guiding a delivery catheter into a center of a lumen in said cuff, and allowing an outer ply to conform against native tissue while an inner ply creates said funnel;

and wherein expanding said lumen of said cuff causes at least one of said end portions to fold.

2. The method of claim 1 further comprising expanding the prosthetic valve within the lumen of the cuff.

3. The method of claim 2 wherein expanding the prosthetic valve within the lumen of the cuff causes the body portion of the cuff to expand.

4. The method of claim 3 wherein causing the body portion to expand causes the body portion to shorten longitudinally.

5. A method of preventing leakage between a prosthetic valve and a vessel wall comprising:

deploying a self-expanding cuff, having a two-ply body and a non-woven fabric layer trapped between the two plies, in the vessel prior to implanting the prosthetic valve;

allowing ends of the cuff to expand and form a seal against the vessel wall while a center body portion of said cuff comprises inwardly-curving sidewalls, wherein at least one of said ends mushrooms when expanded such that a gap is created between the plies of the end, thereby creating a funnel for guiding a delivery catheter into a center of a lumen in said cuff and allowing an outer ply to conform against native tissue while an inner ply creates said funnel;

implanting the prosthetic valve to said inwardly-curving sidewalls after the step of allowing the ends to expand;

such that said cuff forms a seal between said vessel wall and said prosthetic valve;

wherein expanding said lumen of said cuff causes at least one of said ends to fold.

6. The method of claim 5 further comprising expanding the prosthetic valve within the lumen of the cuff.

7. The method of claim 6 wherein expanding the prosthetic valve within the lumen of the cuff causes the body portion of the cuff to expand.

8. The method of claim 7 wherein causing the body portion to expand further comprises causing the body portion to shorten longitudinally.

9. A method of preventing leakage between a prosthetic valve and a vessel wall comprising:

deploying a self-expanding, two-ply cuff in the vessel prior to implanting the prosthetic valve;

allowing ends of the cuff to expand and form a gap between said plies of the ends such that an outer ply forms a seal against the vessel wall while a center body portion of said cuff comprises inwardly-curving sidewalls, wherein at least one of said ends mushrooms when expanded to form said gap, and an inner ply creates a funnel for guiding a delivery catheter into a center of a lumen in said cuff;

implanting the prosthetic valve to said inwardly-curving sidewalls after the step of allowing the ends to expand;

wherein ends of said cuffs are constructed and arranged to fold when said lumen is expanded.

10. The method of claim 9 further comprising expanding the prosthetic valve within the lumen of the cuff.

11. The method of claim 10 wherein expanding the prosthetic valve within the lumen of the cuff causes the body portion of the cuff to expand.

12. The method of claim 11 wherein causing the body portion to expand further comprises causing the body portion to shorten longitudinally.

* * * * *